United States Patent
Kramer et al.

(10) Patent No.: US 8,944,926 B2
(45) Date of Patent: Feb. 3, 2015

(54) TRANSMISSION DEVICE FOR TRANSMITTING A FORCE AND A TORQUE IN A MEDICAL INSTRUMENT

(71) Applicants: Claus Kramer, Immendingen (DE); Jochen Stefan, Wald (DE)

(72) Inventors: Claus Kramer, Immendingen (DE); Jochen Stefan, Wald (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/914,301

(22) Filed: Jun. 10, 2013

(65) Prior Publication Data
US 2013/0344970 A1    Dec. 26, 2013

(30) Foreign Application Priority Data

Jun. 13, 2012 (DE) .......................... 10 2012 105 082

(51) Int. Cl.
| | |
|---|---|
| F16C 1/04 | (2006.01) |
| A61B 17/29 | (2006.01) |
| A61B 17/32 | (2006.01) |
| F16D 3/20 | (2006.01) |
| F16C 1/10 | (2006.01) |
| A61B 17/00 | (2006.01) |

(52) U.S. Cl.
CPC . *F16C 1/04* (2013.01); *A61B 17/29* (2013.01); *A61B 17/32002* (2013.01); *F16D 3/20* (2013.01); *F16C 1/10* (2013.01); *A61B 2017/00526* (2013.01); *A61B 2017/0069* (2013.01); *A61B 2017/2902* (2013.01); *A61B 2017/2903* (2013.01); *A61B 2017/2905* (2013.01); *A61B 2017/2929* (2013.01); *A61B 2017/320032* (2013.01)

USPC ............. 464/147; 29/434; 81/177.6; 464/158

(58) Field of Classification Search
USPC ................. 464/106, 147, 148, 150, 158, 159; 81/177.6, 177.85; 29/434
See application file for complete search history.

(56) References Cited

U.S. PATENT DOCUMENTS

| | | | | |
|---|---|---|---|---|
| 1,091,511 | A | * | 3/1914 | Hayes ............................ 464/148 |
| 1,201,562 | A | * | 10/1916 | Cooper .......................... 464/147 |
| 1,385,713 | A | * | 7/1921 | Robinson, Jr. ................ 464/106 |
| 3,177,683 | A |   | 4/1965 | Olson |
| 5,439,478 | A |   | 8/1995 | Palmer |

(Continued)

FOREIGN PATENT DOCUMENTS

| | | | | |
|---|---|---|---|---|
| DE | 139721 | * | 4/1903 | .................... 464/147 |
| DE | 3923609 A1 | | 1/1990 | |

(Continued)

*Primary Examiner* — Gregory Binda
(74) *Attorney, Agent, or Firm* — St. Onge Steward Johnston & Reens LLC

(57) ABSTRACT

A transmission device for transmitting a force and a torque between a handling device and a tool of a medical instrument includes transmission members interconnected in a hinged manner. A convex coupling portion of a first transmission member is in each case held interlockingly in a concave coupling portion of an adjacent second transmission member in such a way that a rotation of the first transmission member about its longitudinal axis causes a rotation of the second transmission member about its longitudinal axis. A convex coupling portion of a first transmission member is in each case held interlockingly in a concave coupling portion of an adjacent second transmission member in such a way that a tensile force can be transmitted between the first transmission member and the second transmission member.

15 Claims, 3 Drawing Sheets

(56) References Cited

U.S. PATENT DOCUMENTS

| | | |
|---|---|---|
| 2008/0188891 A1 | 8/2008 | Frank et al. |
| 2009/0076511 A1 | 3/2009 | Osman |
| 2010/0087818 A1 | 4/2010 | Cunningham |
| 2011/0303053 A1 | 12/2011 | Schneider et al. |

FOREIGN PATENT DOCUMENTS

| | | |
|---|---|---|
| DE | 10016633 A1 | 10/2001 |
| EP | 2255734 A1 | 12/2010 |
| EP | 2287478 A1 | 2/2011 |
| WO | 2010112608 A1 | 10/2010 |

* cited by examiner

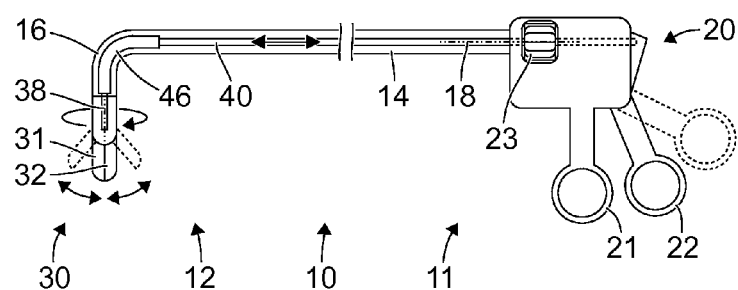
Fig. 1
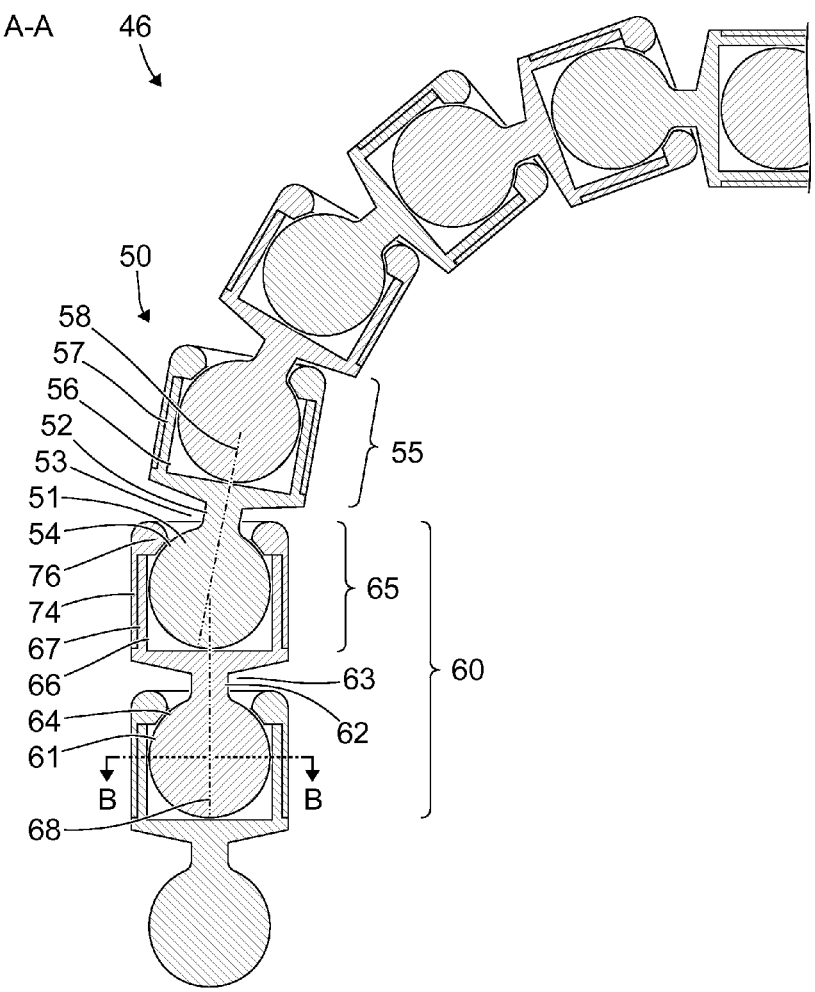
Fig. 2  A-A

TRANSMISSION DEVICE FOR TRANSMITTING A FORCE AND A TORQUE IN A MEDICAL INSTRUMENT

FIELD OF THE INVENTION

The present invention relates to a transmission device for transmitting a force and a torque between a handling device and a tool of a medical instrument, and to a method for producing a transmission device.

BACKGROUND OF THE INVENTION

The expectations placed on medical instruments for microinvasive interventions are constantly increasing. A variety of medical instruments comprising a tool with a gripping or cutting function at the distal end, wherein the tool is rotatable about the longitudinal axis of the shaft, are already available and in widespread use. The gripping function or cutting function and the rotation of the tool can be controlled for example by means of a single transmission rod that transmits longitudinal forces and torques. In addition, a possibility of angling the shaft at a hinge arranged to the proximal side of the tool has been provided more recently. This presupposes a flexibility of the transmission rod in the region of the hinge.

An angle drive device with a multiplicity of movement transmission segments engaging with one another is described in DE 39 23 609 A1. Each movement transmission segment comprises a head portion and a socket portion with a polygonal cross section in each case. The head portion of a movement transmission segment engages in a socket portion of an adjacent movement transmission segment. However the angle drive device does not enable any transmission of tensile forces.

SUMMARY OF THE INVENTION

An object of the present invention is to create an improved transmission device for transmitting a force and a torque between a handling device and a tool of a medical instrument, an improved tool for a medical instrument, an improved medical instrument, and an improved method for producing a transmission device.

This object is achieved by the subjects of the independent claims.

Developments are specified in the dependent claims.

A transmission device for transmitting a force and a torque between a handling device and a tool of a medical instrument comprises transmission members interconnected in a hinged manner, wherein a convex coupling portion of a first transmission member is in each case held interlockingly in a concave coupling portion of an adjacent second transmission member in such a way that a rotation of the first transmission member about its longitudinal axis causes a rotation of the second transmission member about its longitudinal axis, wherein a convex coupling portion of a first transmission member is in each case held interlockingly in a concave coupling portion of an adjacent second transmission member in such a way that a tensile force can be transmitted between the first transmission member and the second transmission member.

The transmission device is designed in particular for a medical instrument for microinvasive surgical interventions and has a shaft between the handling device and tool. The transmission device is provided and designed to transmit a torque and to transmit both compressive forces and tensile forces in the shaft. The transmission members connected in a hinged manner are provided and designed in particular to be arranged in a curved or curvable or flexible or resilient region of the shaft.

So that a rotation of a first transmission member about its longitudinal axis causes a rotation of a second transmission member about its longitudinal axis, the transmission members are coupled to one another in particular in a torsionally rigid manner or are coupled to one another in a manner suitable for the transmission of torques. In particular, the convex coupling portion of a transmission member and the concave coupling portion of an adjacent transmission member each have corresponding polygonal cross sections, for example hexagonal cross sections.

By means of a transmission device having the described features, not only can torques and compressive forces be transmitted, but also tensile forces. For example, this may make it possible to control a rotation and both an opening and a closing of jaw parts of a tool at the distal end of a shaft that can be curved or angled, as is already known from medical instruments with a rigid, straight shaft.

In a transmission device as is described here, in particular a first retaining region is provided on the convex coupling portion of a first transmission member and a second retaining region is provided on the concave coupling portion of an adjacent second transmission member, and the first retaining region and the second retaining region are interlockingly interconnected so as to take up a tensile force between the first transmission member and the second transmission member.

In a transmission device as is described here, and relative to a sectional plane containing the longitudinal axis of the first transmission member, the first retaining region in particular is adjacent to a concave region of the contour of the transmission member, wherein the second retaining region has a substantially convex contour.

The contour of the first retaining region itself in the sectional plane is convex in particular. The second retaining region may have a sliding face, of which the form is matched to the form of the surface of the first retaining region or corresponds thereto. The substantially convex contour of the second retaining region can be concave in the region of the sliding face.

In a transmission device as is described here, the first retaining region on the first transmission member is formed in particular by the edge of a groove, wherein the second retaining region on the second transmission member has the form of a collar, which engages in the groove on the first transmission member.

The groove is in particular a peripheral, radially outwardly open groove occupying the entire periphery of the first transmission member (in particular in a plane perpendicular to the longitudinal axis thereof). The groove in particular forms the above-mentioned concave region of the contour of the first transmission member in the sectional plane containing the longitudinal axis. The first retaining region is formed in particular by a shoulder-shaped region on the first transmission member, which simultaneously is an edge region or a flank of the groove. The second retaining region on the second transmission member in particular has the form of a peripheral, substantially closed and radially inwardly protruding collar. The collar in particular has the form of a complete or almost complete circular ring.

In a transmission device as is described here, the first retaining region is formed in particular by a taper of the first transmission member on a side, facing away from the second transmission member, of the convex coupling portion of the first transmission member.

In a transmission device as is described here, a sleeve, which surrounds the concave coupling portion, in particular forms the radially inwardly protruding collar.

The provision of the radially inwardly protruding collar on a sleeve may enable a cost-effective manufacturing process, in which for example the convex coupling portion for a first transmission member is initially arranged in the sleeve and is then joined to the first transmission member, whereupon the sleeve is joined to the second transmission member.

In a transmission device as is described here, the sleeve in particular comprises a slit, which is parallel to the longitudinal axis of the second transmission member.

In a transmission device as is described here, the first retaining region on the first transmission member is formed in particular by a taper of the first transmission member on a side, facing away from the second transmission member, of the convex coupling portion, wherein the slit in the sleeve has a width that is no smaller than a minimum width of the taper.

The convex coupling portion can be formed in one piece with other regions of the first transmission member, for example by means of machining methods. The taper can then be guided between the convex coupling portion and the rest of the first transmission member through the slit in the sleeve until the collar on the sleeve engages behind the convex coupling portion. The sleeve can then be joined to the second transmission member. The taper in particular has the form of a neck or a waist.

A tool for a medical instrument comprises a transmission device as is described here.

A medical instrument comprises a transmission device as is described here.

In a method for producing a transmission device, a plurality of transmission members each having two coupling portions are provided, wherein one of the plurality of transmission members has a sleeve with a slit extending from the first end to the second end of the sleeve and a radially inwardly protruding collar at the second end of the sleeve. A taper on a convex coupling portion on a first transmission member is guided from the first end through the slit as far as the second end of the sleeve. A concave coupling portion on a second transmission member is introduced into the sleeve, wherein the convex coupling portion on the first transmission member is introduced into the concave coupling portion on the second transmission member. The sleeve is joined to the second transmission member.

The described method can enable simple and cost-effective production of a transmission device, in particular of a transmission device having the above-described features. In particular, all transmission members are identical and each have a sleeve with a slit extending from the first end to the second end of the sleeve. Alternatively, two or more different types of transmission members are provided, wherein each individual transmission member may have, at each end, at one end or at neither end, a sleeve with a radially inwardly protruding collar.

BRIEF DESCRIPTION OF THE DRAWINGS

Embodiments are explained in greater detail hereinafter with reference to the accompanying figures, in which:

FIG. 1 shows a schematic illustration of a medical instrument;

FIG. 2 shows a schematic sectional illustration of a flexible portion of transmission device along sectional plane A-A;

DETAILED DESCRIPTION OF THE INVENTION

Figure 3:
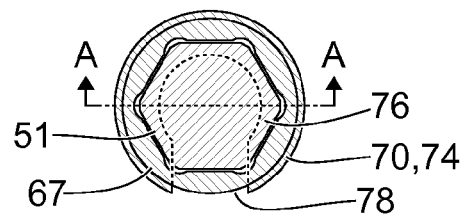
FIG. 3 shows a further schematic sectional illustration of the flexible portion from FIG. 2 along sectional plane B-B.

FIG. 1 shows a schematic illustration of a medical instrument 10 having a proximal end 11 and a distal end 12, between which a shaft 14 with a hinge 16 extends. The shaft 14 is in particular rigid and straight on the proximal side of the hinge 16 and has a longitudinal axis 18. The hinge 16 is formed by a flexible or resilient portion of the shaft 14 or by a hinged connection of two rigid portions of the shaft 14.

At the proximal end 11, the medical instrument 10 has a handling device 20 with a stationary grip part 21 and a movable grip part 22. The movable grip part 22 is in particular pivotable about a pivot axis perpendicular to the drawing plane in FIG. 1. A first position of the movable grip part 22 is illustrated in FIG. 1 by solid lines. A second position of the movable grip part 22 is illustrated in FIG. 1 by dashed lines. The handling device 20 further has a turning wheel 23, which is rotatable about the longitudinal axis 18 of the shaft 14.

At the distal end 12 of the medical instrument 10, a tool 30 with two pivotable jaw parts 31, 32 is provided. In FIG. 1, it is indicated by two arrows that the pivotable jaw parts 31, 32 can each be pivoted about an assigned pivot axis perpendicular to the drawing plane in FIG. 1 between closed positions and open positions. The closed positions are illustrated in FIG. 1 by solid lines, and the open positions are illustrated in FIG. 1 by dashed lines. Furthermore, the tool 30 with the jaw parts 31, 32 is rotatable about an axis of rotation 38, which in particular is the longitudinal axis of the tool 30.

The handling device 20 at the proximal end 11 and the tool 30 at the distal end 12 of the medical instrument 10 are coupled by means of a transmission device 40, in particular a transmission rod, in the shaft 14. The transmission device 40 comprises a flexible portion 46, which is explained below with reference to FIGS. 2 to 6. The transmission device 40 in particular couples the movable grip part 22 of the handling device 20 and the turning wheel 23 on the handling device 20 on the one hand to the tool 30 on the other hand.

In particular, a manual movement of the movable grip part 22 on the handling device 20 is transmitted to the jaw parts 31, 32 by an axial movement of the transmission device 40 parallel to the longitudinal axis 18 of the medical instrument 10 and, on the distal side of the flexible portion 46, parallel to the axis of rotation 38 of the tool 30 and causes opening or closing pivot movements of the jaw parts 31, 32. A rotation of the turning wheel 23 about the longitudinal axis 18 is transmitted to the tool 30 by a rotation of the transmission device 40 about the longitudinal axis 18 and, on the distal side of the flexible portion 46, about the longitudinal axis 38 of the tool 30 and causes a rotation of the tool 30 about its axis of rotation 38.

For transmission, with little play and little friction, of longitudinal forces and torques, the transmission device 40 is mounted in the shaft 14 with little play and little friction and is rigid or unresilient with regard to compressive forces and tensile forces and is also torsionally rigid or rigid in terms of a torsion about its longitudinal axis. This is also true in particular for the flexible portion 46.

FIG. 2 shows a schematic sectional illustration of an exemplary embodiment of the flexible portion 46 of the transmission device 40 from FIG. 1. The sectional plane A-A in FIG.

2 is parallel to the drawing plane in FIG. 1 and in particular contains the longitudinal axis 18 of the shaft 14 and the longitudinal axis 38 of the tool 30. The flexible portion 46 comprises a plurality of transmission members 50, 60, which are identical in terms of design and of which the longitudinal axes 58, 68 likewise lie in the sectional plane A-A in FIG. 2.

Each transmission member 50, 60 comprises a convex coupling portion 51, 61 and a concave coupling portion 55, 65. In the sectional plane A-A in FIG. 2, the convex coupling portions 51, 61 each have a substantially circular cross section. Each transmission member 50, 60 has a taper or a neck 52, 62 or a peripheral groove 53, 63 between the convex coupling portion 51, 61 and the concave coupling portion 55, 65.

The concave coupling portions 55, 65 comprise recesses 56, 66, which, in the sectional plane A-A, each have a substantially rectangular cross section and are surrounded by a wall 57, 67. Each concave coupling portion 55, 65 further comprises a sleeve 70. Each sleeve 70 has a substantially cylindrical wall 74, which surrounds the wall 57, 67 around the recess 56, 66 like a casing. The sleeve 70 further has a radially inwardly protruding collar 76. The sleeves 70 are joined, in particular welded, to the concave coupling portions 55, 65.

In each case, the convex coupling portion 51 on a first transmission member 50 engages in the concave coupling portion 65 on a second, adjacent transmission member 60. The collar 76 on the sleeve 70 of the concave coupling portion 65 of the second transmission member 60 engages in part in the groove 53 on the first transmission member 50 and bears against a shoulder-shaped region 54 on the convex coupling portion 51 of the first transmission member 50. The sliding face provided on the collar 76 for bearing against the shoulder-shaped region 54 on the convex coupling portion 51 of the first transmission member 50 has, in accordance with the substantially spherical cross section of the convex coupling portion 51 in the sectional plane A-A, in particular the form of an annular cutout of a spherical surface.

By virtue of the at least partial engagement of the collar 76 of a transmission member 60 in the groove 53 on the adjacent transmission member 50 or by virtue of the bearing of the collar 76 of a transmission member 60 against the shoulder-shaped region 54 on the convex coupling portion 51 of the adjacent transmission member 50, it is not only compressive forces that can be transmitted between the transmission members 50, 60, but also tensile forces. Tensile forces can therefore also be transmitted through the entire flexible portion 46 of the transmission device 40. The illustration in FIG. 2 shows that the interlocking coupling of the transmission members 50, 60 is hinged. The longitudinal axes 58, 68 of adjacent transmission members 50, 60 can therefore be tilted relative to one another within a predetermined angular range.

FIG. 3 shows a further schematic sectional illustration of the flexible portion 46 from FIG. 2. The position of the sectional plane B-B illustrated in FIG. 3 perpendicular to the longitudinal axis 68 of a transmission member 60 is indicated in FIG. 2. The position of the sectional plane A-A illustrated in FIG. 2 is indicated in FIG. 3.

In the sectional plane B-B, both the convex coupling portion 51 and the inner surface of the wall 67 each have a substantially hexagonal cross section. The substantially hexagonal cross sections, corresponding to one another, of the convex coupling portion 51 of the first transmission member 50 and of the wall 67 of the concave coupling portion 65 of the second transmission member 60 cause an interlocking coupling of the transmission members 50, 60, which enables transmission of a torque between the transmission members 50, 60.

The outer surface of the wall 67 and the wall 74 of the sleeve 70 each have substantially the form of a circular-cylinder casing. Deviating from this, the sleeve 70 has a slit 78, of which the width in the sectional plane B-B is at least as large as the diameter of the neck 52 (see FIG. 2). The radially inner contour of the collar 76 of the sleeve 70 and also of the extension of the slit 78 into the collar 76 is illustrated in a dashed line. The collar 76 therefore does not have the form of a closed circular ring, but, deviating from this, a gap corresponding to the slit 78.

Figure 4:
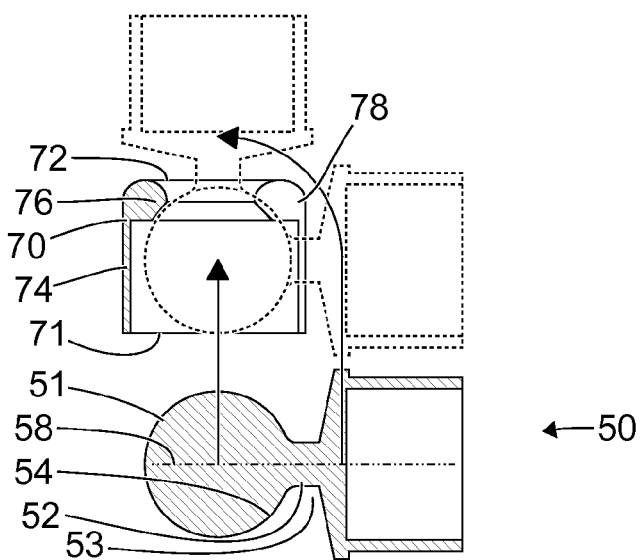
FIG. 4 shows a further schematic sectional illustration of coupling members from FIGS. 2 and 3.

FIG. 4 shows a schematic sectional illustration of a first transmission member 50 and of a sleeve 70 of a second transmission member, of which further components are not visible in FIG. 4. The sectional plane in FIG. 4 is perpendicular to the sectional plane A-A in FIG. 2 and perpendicular to the sectional plane B-B in FIG. 3 and contains the longitudinal axis 58 of the transmission member 50. The sectional plane in FIG. 4 in particular runs in the middle of the slit 78 in the sleeve 70 and parallel to the edges thereof.

The transmission member 50 is shown by solid lines and hatched cross-sectional area in an initial position, in which the longitudinal axis 58 of the transmission member 50 is perpendicular to the longitudinal axis of the sleeve 70. From this initial position, the convex coupling portion 51 of the transmission member 50 is introduced from the first end 71 thereof into the sleeve 70, by means of the movement purely in translation indicated by the straight arrow, until the convex coupling portion 51 of the transmission member 50 bears substantially against the collar 76 of the sleeve 70, and the neck 52 of the transmission member 50 is arranged in the slit 78 in the sleeve 70. The configuration thus achieved is indicated by dashed contours.

As is indicated in FIG. 4 by a curved arrow, the transmission member 50 is then pivoted about an axis perpendicular to the drawing plane in FIG. 4 and, in so doing, is pivoted about the convex coupling portion 51 until the longitudinal axis of the transmission member 50 is substantially parallel to the longitudinal axis of the sleeve 70. The configuration thus achieved is likewise indicated by dashed contours. In this configuration, the neck 52 of the transmission member 50 is no longer arranged in the slit 78 in the sleeve 70, but substantially in the middle of the collar 76 at the second end 72 of the sleeve 70.

Figure 5:
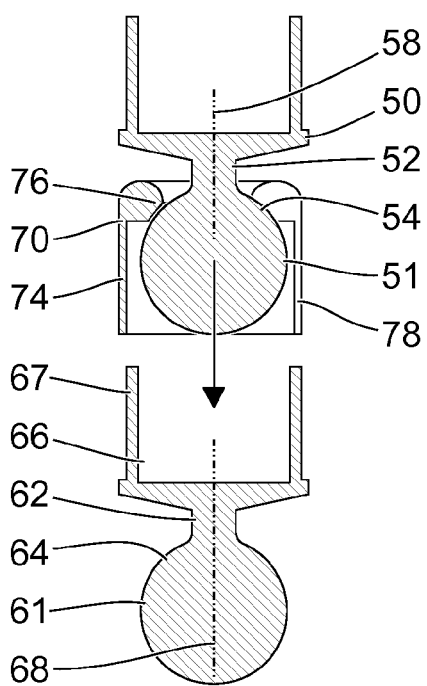
FIG. 5 shows a further schematic sectional illustration of the coupling members from FIG. 4.

FIG. 5 shows a further schematic sectional illustration of the transmission member 50 and of the sleeve 70 from FIG. 4 in the configuration that is present at the end of the movement described with reference to FIG. 4. The transmission member 50 and the sleeve 70 are illustrated together with a further transmission member 60. A movement of the transmission member 50 together with the sleeve 70 relative to the further transmission member 60 is indicated by a straight arrow. With this movement, the convex coupling portion 51 of the transmission member 50 is introduced into the recess 66 on the further transmission member 60. At the same time, the sleeve 70 is drawn over the wall 67 around the recess 66 on the further transmission member 60, or the wall 67 is introduced into the sleeve 70. When the configuration illustrated in FIG. 2 is reached, the sleeve 70 and the further transmission member 60 are joined, in particular by welding, soldering or adhesive bonding.

Figure 6:
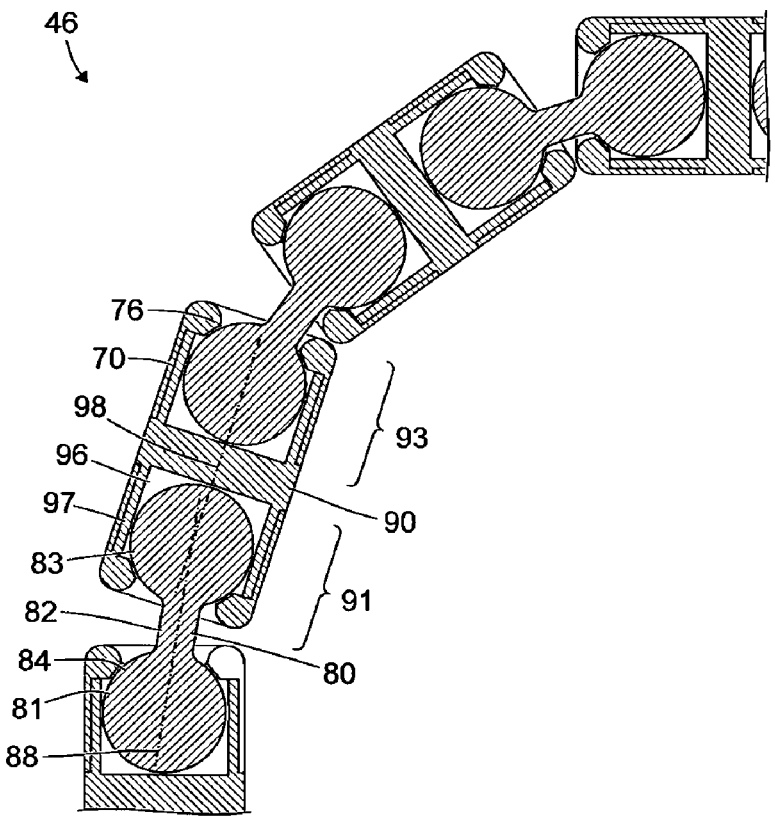
FIG. 6 shows a schematic sectional illustration of a further flexible portion of a transmission device.

FIG. 6 shows a schematic sectional illustration of a further exemplary embodiment of the flexible portion 46 of the transmission device 40 from FIG. 1. The sectional plane in FIG. 6 corresponds to the sectional plane in FIG. 2.

The exemplary embodiment in FIG. 6 differs from the exemplary embodiment in FIGS. 2 to 5 in that not all transmission members are identical. Instead, transmission members 80, 90 of two different types or designs are provided and are arranged alternately. A transmission member 80 of the first type has two convex coupling portions 81, 83 with a taper or a neck 82 between the convex coupling portions. A transmission member 90 of the second type has two concave coupling portions 91, 93.

Each individual convex coupling portion 81, 83 of a transmission member 80 of the first type corresponds in terms of form and function to the convex coupling portion 51, 61 of a transmission member 50, 60 in the exemplary embodiment from FIGS. 2 to 5. Each individual concave coupling portion 91, 93 of a transmission member 90 of the second type corresponds in terms of spatial form and function to the concave coupling portion 55, 65 of a transmission member 50, 60 in the exemplary embodiment from FIGS. 2 to 5. In particular, each transmission member 90 of the second type therefore has two sleeves 70. The sleeves correspond to the exemplary embodiment in FIGS. 2 to 5.

The interlocking, hinged coupling between a convex coupling portion 81, 83 of a transmission member of the first type and a concave coupling portion 91, 93 of a transmission member 90 of the second type corresponds to the interlocking mechanical coupling between a convex coupling portion 51 of a transmission member and a concave coupling portion 65 of an adjacent transmission member 60 in the exemplary embodiment illustrated above with reference to FIGS. 2 to 5. The exemplary embodiment, illustrated in FIG. 6, of the flexible portion 46 of the transmission device 40 therefore enables transmission of compressive forces and tensile forces and also of torques, similarly to the exemplary embodiment illustrated above with reference to FIGS. 2 to 5. The flexible portion 46 according to the exemplary embodiment illustrated in FIG. 6 can also be produced in accordance with the method presented above with reference to FIGS. 4 and 5 for the exemplary embodiment in FIGS. 2 to 5.

Figure 7:
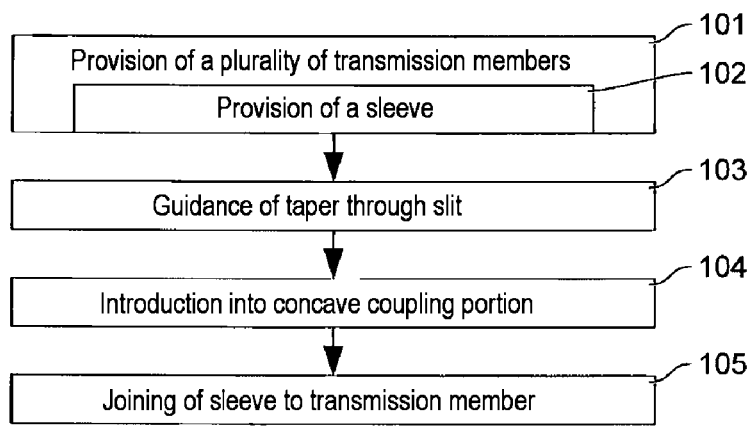
FIG. 7 shows a schematic flow diagram.

FIG. 7 shows a schematic flow diagram of a method for producing a transmission device. Although the method is also suitable for producing a transmission device having features that differ from those presented above with reference to FIGS. 1 to 6, reference signs from FIGS. 1 to 6 will be used hereinafter by way of example to facilitate comprehension.

In a first step 101, a plurality of transmission members 50, 60; 80, 90 each having two coupling portions 51, 61, 55, 65; 81, 83, 91, 93 are provided. The provision of the plurality of transmission members comprises provision 102 of a sleeve 70 as a component of one of the transmission members 50, 60; 80, 90. The sleeve 70 provided in the second step 102 has a slit 78, which extends from the first end 71 to the second end 72 of the sleeve 70. The sleeve 70 further has a radially inwardly protruding collar 76 at the second end 72 of the sleeve 70.

In a third step 103, a taper or a neck 52; 82 on a convex coupling portion 51; 81, 83 on a transmission member 50; 80 is guided from the first end 71 through the slit 78 as far as the second end 72 of the sleeve 70. The third step 103 is performed for example as presented above with reference to FIG. 4.

In a fourth step 104, the convex coupling portion 51; 81, 83 on the first transmission member 50; 80 is introduced into the concave coupling portion 65; 91, 93 on the second transmission member 60; 90. Here, the concave coupling portion 65; 91, 93 on the second transmission member 60; 90 is simultaneously introduced into the sleeve 70. In a fifth step 105, the sleeve 70 is joined, in particular welded, soldered or adhesively bonded, to the second transmission member 60; 90.

REFERENCE SIGNS 10 medical instrument
11 proximal end of the medical instrument 10
12 distal end of the medical instrument 10
14 shaft of the medical instrument 10
16 hinge on the shaft 14
18 longitudinal axis of the medical instrument 10
20 handling device at the proximal end 11 of the medical instrument 10
21 stationary grip part of the handling device 20
22 movable grip part of the handling device 20
23 turning wheel on the handling device 20
30 tool at the distal end 12 of the medical instrument 10
31 first jaw part on the tool 30
32 second jaw part on the tool 30
38 axis of rotation of the tool 30
40 transmission device
46 flexible portion of the transmission device 40
50 transmission member
51 convex coupling portion of the transmission member 60
52 neck of the transmission member 50
53 groove on the transmission member 50
54 shoulder-shaped region on the convex coupling portion 51
55 concave coupling portion on the transmission member 50
56 recess on the concave coupling portion 55
57 wall around the recess 56
58 longitudinal axis of the transmission member 50
60 transmission member
61 convex coupling portion of the transmission member 60
62 neck of the transmission member 60
63 groove on the transmission member 60
64 shoulder-shaped region on the convex coupling portion 61
65 concave coupling portion on the transmission member 60
66 recess on the concave coupling portion 65
67 wall around the recess 66
68 longitudinal axis of the transmission member 60
70 sleeve of the transmission member 60
71 first end of the sleeve 70
72 second end of the sleeve 70
74 cylindrical wall of the sleeve 70
76 edge at the second end 72 of the sleeve 70
78 slit in the sleeve 70
80 transmission member of a first type
81 first convex coupling portion of the transmission member 80
82 neck of the transmission member 80
83 second convex coupling portion of the transmission member 80
84 shoulder-shaped region on the first convex coupling portion 81
88 longitudinal axis of the transmission member 80
90 transmission member of a second type
91 first concave coupling portion of the transmission member 90
93 second concave coupling portion of the transmission member 90
96 recess on the concave coupling portion 95
97 wall around the recess 96
98 longitudinal axis of the transmission member 90
101 first step (provision)
102 second step (provision)
103 third step (guidance through)
104 fourth step (introduction)
105 fifth step (joining)

The invention claimed is:

1. A transmission device for transmitting a force and a torque between a handling device and a tool of a medical instrument, said transmission device comprising:
   transmission members interconnected in a hinged manner, each transmission member having a convex coupling portion, a concave coupling portion, and a sleeve surrounding the concave coupling portion and forming a radially inwardly protruding collar,
   wherein a convex coupling portion of a first transmission member is in each case held interlockingly in a concave coupling portion of an adjacent second transmission member in such a way that a rotation of the first transmission member about its longitudinal axis causes a rotation of the second transmission member about its longitudinal axis,
   wherein a convex coupling portion of a first transmission member is in each case held interlockingly in a concave coupling portion of an adjacent second transmission member in such a way that a tensile force can be transmitted between the first transmission member and the second transmission member.

2. The transmission device according to claim 1, wherein a first retaining region provided on the convex coupling portion of a first transmission member and a second retaining region is provided on the concave coupling portion of an adjacent second transmission member, and the first retaining region and the second retaining region are interlockingly interconnected so as to take up a tensile force between the first transmission member and the second transmission member.

3. The transmission device according to claim 2, wherein, relative to a sectional plane containing the longitudinal axis of the first transmission member, the first retaining region is adjacent to a concave region of the contour of the transmission member, and the second retaining region has a substantially convex contour.

4. The transmission device according to claim 2, wherein the first retaining region on the first transmission member is formed by the edge of a groove, and the second retaining region on the second transmission member has the form of a collar, which engages in the groove on the first transmission member.

5. The transmission device according to claim 4, wherein the sleeve comprises a slit, which is parallel to the longitudinal axis of the second transmission member.

6. The transmission device according to claim 5, wherein the first retaining region on the first transmission member is formed by a taper of the first transmission member on a side, facing away from the second transmission member, of the convex coupling portion, and the slit in the sleeve has a width that is no smaller than a minimum width of the taper.

7. The transmission device according to claim 1, wherein the transmission members comprise at least three transmission members.

8. The transmission device according to claim 1, wherein the transmission members are identical.

9. A tool for a medical instrument comprising a transmission device according to claim 1.

10. A medical instrument comprising a transmission device according to claim 1.

11. A method for producing a transmission device according to claim 1, said method comprising the following steps:
   provision of a plurality of transmission members each having two coupling portions, wherein one of the plurality of transmission members has a sleeve with a slit extending from the first end to the second end of the sleeve and with a radially inwardly protruding collar at the second end of the sleeve;
   guidance of a taper on a convex coupling portion on a first transmission member from the first end through the slit as far as the second end of the sleeve;
   introduction of a concave coupling portion on a second transmission member into the sleeve, wherein the convex coupling portion on the first transmission member is introduced into the concave coupling portion on the second transmission member;
   joining of the sleeve to the second transmission member.

12. The method for producing a transmission device according to claim 11, further comprising the step of incorporating the transmission device into a tool for a medical instrument.

13. The method for producing a transmission device according to claim 11, further comprising the step of incorporating the transmission device into a medical instrument.

14. The method for producing a transmission device according to claim 11, wherein the plurality of transmission members comprises at least three transmission members.

15. The method for producing a transmission device according to claim 11, wherein the plurality of transmission members are identical.

* * * * *